United States Patent
Ghosal et al.

(10) Patent No.: US 7,312,223 B2
(45) Date of Patent: Dec. 25, 2007

(54) METABOLITE OF XANTHINE PHOSPHODIESTERASE 5 INHIBITOR AND DERIVATIVES THEREOF USEFUL FOR TREATMENT OF ERECTILE DYSFUNCTION

(75) Inventors: Anima Ghosal, Edison, NJ (US); Wei Tong, New City, NY (US); Swapan K. Chowdhury, Warren, NJ (US); Shmuel Zbaida, East Brunswick, NJ (US); Mark A. Wirth, Neshanic Station, NJ (US); Kevin B. Alton, Cedar Knolls, NJ (US); James E. Patrick, Aiken, SC (US); Craig D. Boyle, Branchburg, NJ (US); Andrew Stamford, Chatham Township, NJ (US)

(73) Assignee: Schering Corporation, Kenilworth, NJ (US)

( * ) Notice: Subject to any disclaimer, the term of this patent is extended or adjusted under 35 U.S.C. 154(b) by 440 days.

(21) Appl. No.: 10/901,574

(22) Filed: Jul. 29, 2004

(65) Prior Publication Data

US 2005/0026939 A1    Feb. 3, 2005

Related U.S. Application Data

(60) Provisional application No. 60/492,218, filed on Jul. 31, 2003.

(51) Int. Cl.
C07D 473/06 (2006.01)
A61K 31/522 (2006.01)
A61P 9/10 (2006.01)
A61P 9/12 (2006.01)

(52) U.S. Cl. .................. 514/263.34; 544/271; 544/272; 514/263.35; 514/263.36

(58) Field of Classification Search ........... 514/263.34, 514/263.35, 263.36; 544/217, 272
See application file for complete search history.

(56) References Cited

U.S. PATENT DOCUMENTS

| | | | |
|---|---|---|---|
| 5,393,755 A | 2/1995 | Neustadt et al. | |
| 5,409,934 A * | 4/1995 | Smith et al. | 514/263.33 |
| 5,939,419 A | 8/1999 | Tulshian et al. | |
| 6,821,978 B2 | 11/2004 | Chackalamannil et al. | |

FOREIGN PATENT DOCUMENTS

| WO | WO 92/05175 | 4/1992 |
|---|---|---|
| WO | WO 93/23401 | 11/1993 |
| WO | WO 02/24698 | 3/2002 |
| WO | WO 03/101991 | 12/2003 |
| WO | WO 03/101992 | 12/2003 |

OTHER PUBLICATIONS

Ahn, H.S., et.al., "Potent Tetracyclic Guanine Inhibitors . . . ", Journal of Medicinal Chem., Am. Chem. Soc. vol. 40, No. 14, pp. 2196-2210 (1997).
Wang, Y., et.al., "Design and Synthesis of Xanthine Analogues . . . ", Bioorganic and Medicinal Chemistry Letter, vol. 12, No. 21, pp. 3149-3152, (2002).
International Search Report for PCT/US2004/024525; mailed Dec. 21, 2004; 5 pages.

\* cited by examiner

*Primary Examiner*—Mark L. Berch
(74) *Attorney, Agent, or Firm*—Gerard E. Reinhardt

(57) ABSTRACT

The present invention is directed to a metabolite of a xanthine Phosphodiesterase type 5 inhibitor having the following structure

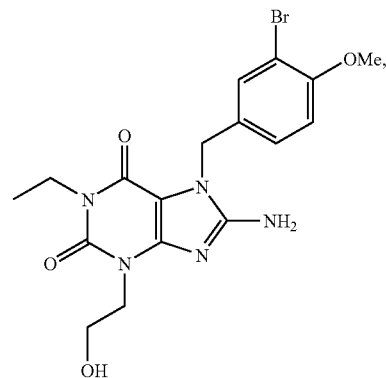

derivatives, and formulations thereof, and processes for preparing the same.

Further disclosed are methods of treating a physiological disorder, symptom or disease in a patient, comprising administering to the patient an effective amount of the above compound, wherein the physiological disorder, symptom or disease is a urogenital, cardiovascular, cerebrovascular or peripheral vascular disorder, angina pectoris, hypertension, restenosis post angioplasty, endarterectomy, stent introduction, cerebral stroke, a respiratory tract disorder such as an allergic condition associated with atopy, pulmonary hypertension, an ischemic heart disorder, impaired glucose tolerance, diabetes and its related complication, insulin resistance syndrome, hyperglycemia, polycystic ovarian syndrome, a glomerular disorder, renal insufficiency, nephritis, a tubular interstitial disorder, an autoimmune disorder, glaucoma, intestinal motility, cachexia or cancer.

15 Claims, 2 Drawing Sheets

METABOLITE OF XANTHINE PHOSPHODIESTERASE 5 INHIBITOR AND DERIVATIVES THEREOF USEFUL FOR TREATMENT OF ERECTILE DYSFUNCTION

CROSS-REFERENCE TO RELATED APPLICATION

This application claims benefit to provisional application 60/492,218 filed Jul. 31, 2003.

BACKGROUND

1. Field of the Invention

The present invention relates to a metabolite of a xanthine Phosphodiesterase type 5 ("PDE 5") inhibitor useful for treatment of erectile dysfunction, and derivatives, formulations and processes related thereto.

2. Background

U.S. patent application Ser. No. 09/940,760, incorporated herein by reference, teaches a class of xanthine PDE 5 inhibitor compounds useful for the treatment of impotence. U.S. Pat. Nos. 5,939,419 and 5,393,755, both of which are incorporated herein by reference, disclose polycyclic guanine PDE 5 derivatives that are useful for the treatment of cardiovascular and pulmonary disorders.

Certain xanthine/guanine PDE 5 inhibitors have been found to be useful for treating cardiovascular and pulmonary disorders, while others have been found useful for treating urological disorders, including male erectile dysfunction. Generally, it has been suggested that PDE 5 inhibitors may be useful for treating physiological disorders, symptoms or diseases that include urogenital, cardiovascular, cerebrovascular and peripheral vascular disorders, angina pectoris, hypertension, restenosis post angioplasty, endarterectomy, stent introduction, cerebral stroke, respiratory tract disorders such as allergic conditions associated with atopy, pulmonary hypertension, ischemic heart disorders, impaired glucose tolerance, diabetes and its related complications, insulin resistance syndrome, hyperglycemia, polycystic ovarian syndrome, glomerular disorders, renal insufficiency, nephritis, tubular interstitial disorders, autoimmune disorders, glaucoma, intestinal motility, cachexia or cancer.

In the treatment of erectile dysfunction, it is believed that PDE 5 inhibitors are beneficial therapeutic agents because they elevate cGMP levels in the human body. This action facilitates corpus cavernosum smooth muscle relaxation, which provides an increased flow of blood therein and results in an erection. This makes PDE 5 inhibitors especially useful for treating impotence and other types of diseases that are affected by cGMP levels.

In U.S. patent application Ser. No. 09/940,760, Compound 114 in Table II, herein identified as Compound A, was disclosed as having PDE 5 inhibitory activity.

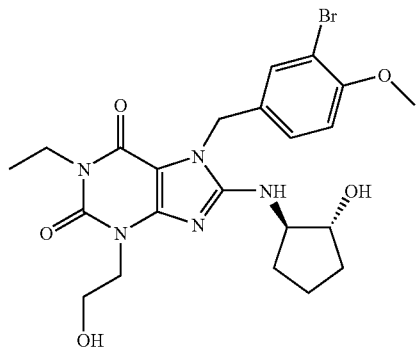

Compound A

SUMMARY OF INVENTION

In one embodiment, the present invention is directed to Compound C represented by the formula:

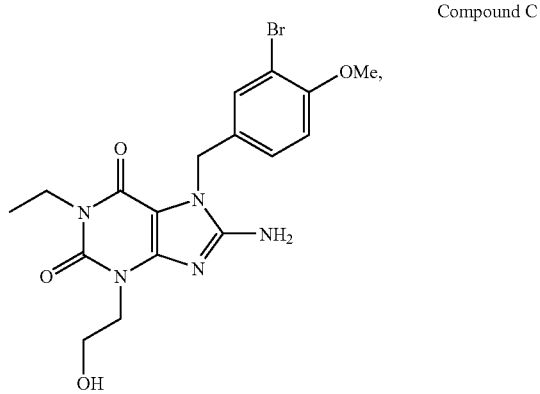

Compound C or pharmaceutically acceptable salts, solvates or esters thereof.

In other embodiments, the invention is directed to derivatives of Compound C, which can be described by the following structure:

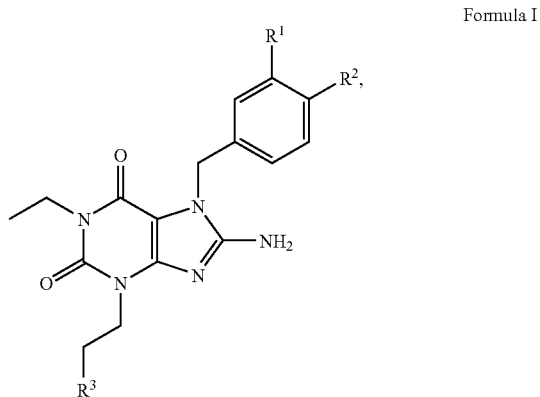

Formula I wherein $R^1$, $R^2$ and $R^3$ are independently selected from the group consisting of H, OH, $OR^4$, F, Cl, Br, $NH_2$, $NHR^4$, $(NR^4)_2$, —COOH, and —$CONH_2$, and $R^4$ is independently selected from the group consisting of H, —$CH_3$, —$C_2H_5$, isopropyl, and n-$C_3H_7$.

In further embodiments, $R^1$ is Br.

In further embodiments, $R^2$ is OMe.

In further embodiments, $R^3$ is OH.

In other embodiments, the present invention is directed to a pharmaceutical composition comprising a therapeutically effective amount of Compound C, or a derivative thereof, in combination with a pharmaceutically acceptable carrier.

In other embodiments, the present invention is directed to a purified and isolated form of Compound C or a derivative thereof.

In other embodiments, the present invention is directed to a method for treating a physiological disorder, symptom or disease in a patient, comprising administering to the patient an effective amount of Compound C or a derivative thereof, wherein the physiological disorder, symptom or disease is a urogenital, cardiovascular, cerebrovascular or peripheral vascular disorder, angina pectoris, hypertension, restenosis post angioplasty, endarterectomy, stent introduction, cerebral stroke, a respiratory tract disorder such as an allergic condition associated with atopy, pulmonary hypertension, an ischemic heart disorder, impaired glucose tolerance, diabetes or any of its related complications, insulin resistance syndrome, hyperglycemia, polycystic ovarian syndrome, a glomerular disorder, renal insufficiency, nephritis, a tubular interstitial disorder, an autoimmune disorder, glaucoma, intestinal motility, cachexia or cancer.

In another embodiment, the present invention is directed to a method for elevating a cGMP level in a patient in need of the treatment, comprising administering to the patient an effective amount of Compound C or a derivative thereof.

In another embodiment, the present invention is directed to a method for treating an erectile dysfunction in a patient in need of the treatment, comprising administering to the patient an effective amount of Compound C or a derivative thereof.

In another embodiment, the present invention is directed to a method for treating an erectile dysfunction in a patient in need of the treatment, comprising administering to the patient an effective amount of a prodrug form of Compound C or a derivative thereof.

In another embodiment, the present invention is directed to a method for producing Compound C, by reacting a solution of Compound B in EtOH and aqueous $NH_4Cl$ in the presence of $NH_4OH$:

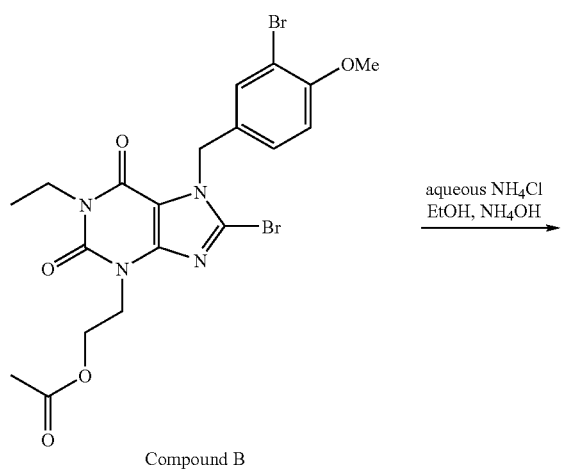

Compound B

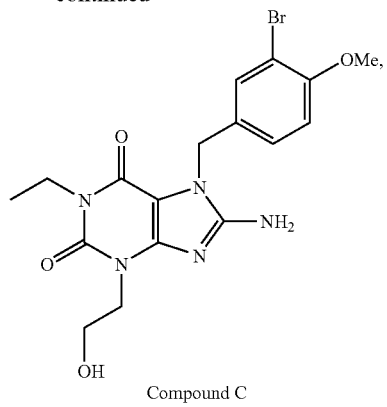

Compound C wherein, Compound B is dissolved in EtOH and saturated $NH_4Cl$, $NH_4OH$ is added to adjust the pH of the solution to about 8, and the solution is heated at about 160° C. for about 9 days.

DETAILED DESCRIPTION OF INVENTION

Figure 1:
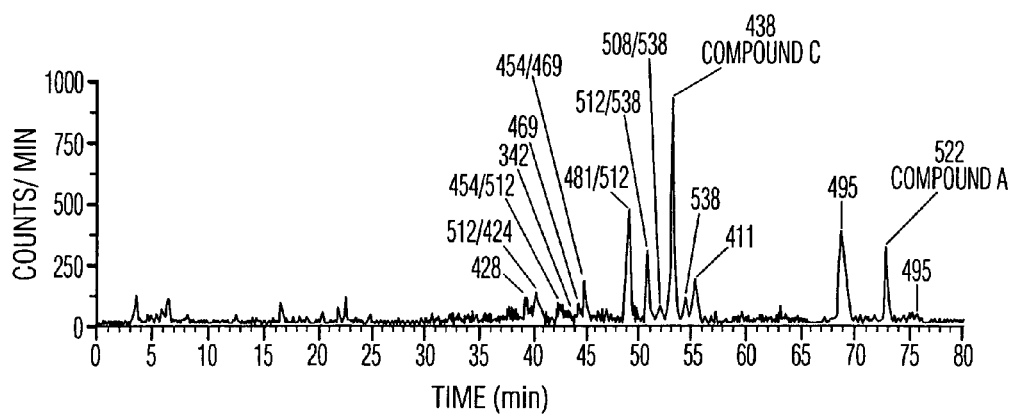
FIG. 1 shows a radiometric profile of the incubated drug and metabolites following a 120 min. incubation of Compound A with cytochrome P450 3A4 (CYP3A4) and a NADPH-generating system.

As used above, and throughout the specification, the following terms, unless otherwise indicated, shall be understood to have the following meanings:

"Patient" includes both humans and animals.

"Mammal" means humans and other mammalian animals.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting PDE 5 and thus producing the desired therapeutic, ameliorative, inhibitory or preventative effect.

The Compound C and the compounds of Formula I can form salts which are also within the scope of this invention. Reference to Compound C or a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when Compound C or a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of Compound C or the compounds of the Formula I may be formed, for example, by reaction with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quaternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

"Composition" is intended to encompass a product comprising the specified ingredients in the specified amounts, as well as any product which results, directly or indirectly, from combination of the specified ingredients in the specified amounts.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds.

By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "isolated" or "in isolated form" for a compound refers to the physical state of said compound after being isolated from a synthetic process or natural source or combination thereof. The term "purified" or "in purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and claims herein is assumed to have the sufficient number of hydrogen atom(s) to satisfy the valences.

"Halogen" means fluorine, chlorine, bromine, or iodine. Preferred are fluorine, chlorine and bromine.

When any variable (e.g., aryl, heterocycle, $R^2$, etc.) occurs more than one time in any constituent or in Formula I, its definition on each occurrence is independent of its definition at every other occurrence.

Unless otherwise indicated, all quantitative measures of physical parameters stated herein, e.g., temperature, mass, volume, concentration, are understood to include a reasonable scope of variation from the stated nominal values.

NADPH is the reduced form of $NADP^+$, which stands for β-Nicotinamide Adenine Dinucleotide Phosphate. The general drug oxidation pathway by cytochrome P450 is described in the scheme below (S=Substrate):

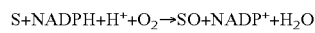

During this process, which requires the oxidation of NADPH to $NADP^+$, one atom of oxygen is incorporated into the substrate (SO, oxidation) while the other oxygen atom is reduced to form water.

General Description

A metabolite of PDE 5 inhibitor Compound A may be useful for treating male (erectile) and female sexual dysfunction and other physiological disorders. A representative compound of this invention is presented below as Compound C ($IC_{50}$ 71 nM):

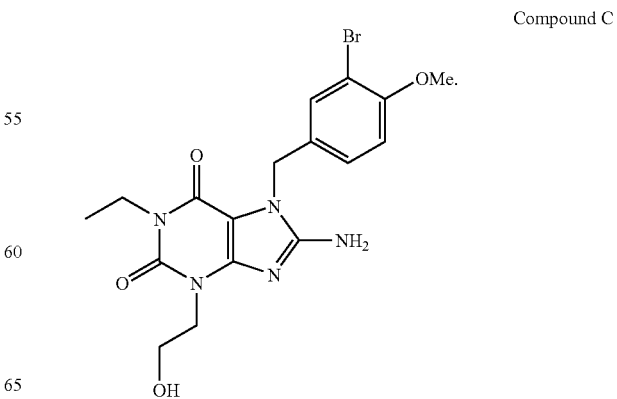

Compound C represents one of the major circulating metabolites following single administration of Compound A (100 mg PO) to humans (P02407). Its chemical name is 8-Amino-7-[(3-Bromo-4-Methoxyphenyl)Methyl]-1-Ethyl-3,7-Dihydro-3-(2-Hydroxyethyl)-1H-Purine-2,6-Dione.

Along with other metabolites of Compound A, this metabolite was originally identified from human in vitro enzyme preparations and later it was also identified from human in vivo samples. This metabolite was found to be a prominent circulating metabolite in human (in vivo) following a single oral administration.

Procedure for Chemical Synthesis of Compound C

The structure of Compound B is disclosed in U.S. patent application Ser. No. 10/449,526, which is incorporated by reference thereto. In that application, Compound B is referred to as Compound 7A.

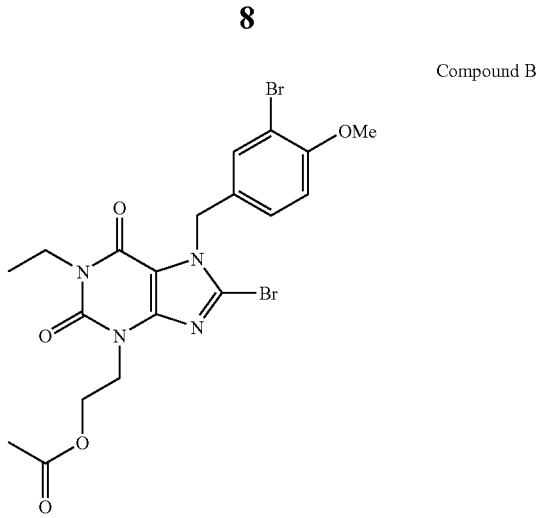

U.S. patent application Ser. No. 10/449,526 also discloses the following scheme for the synthesis of Compound B (labeled "7A"):

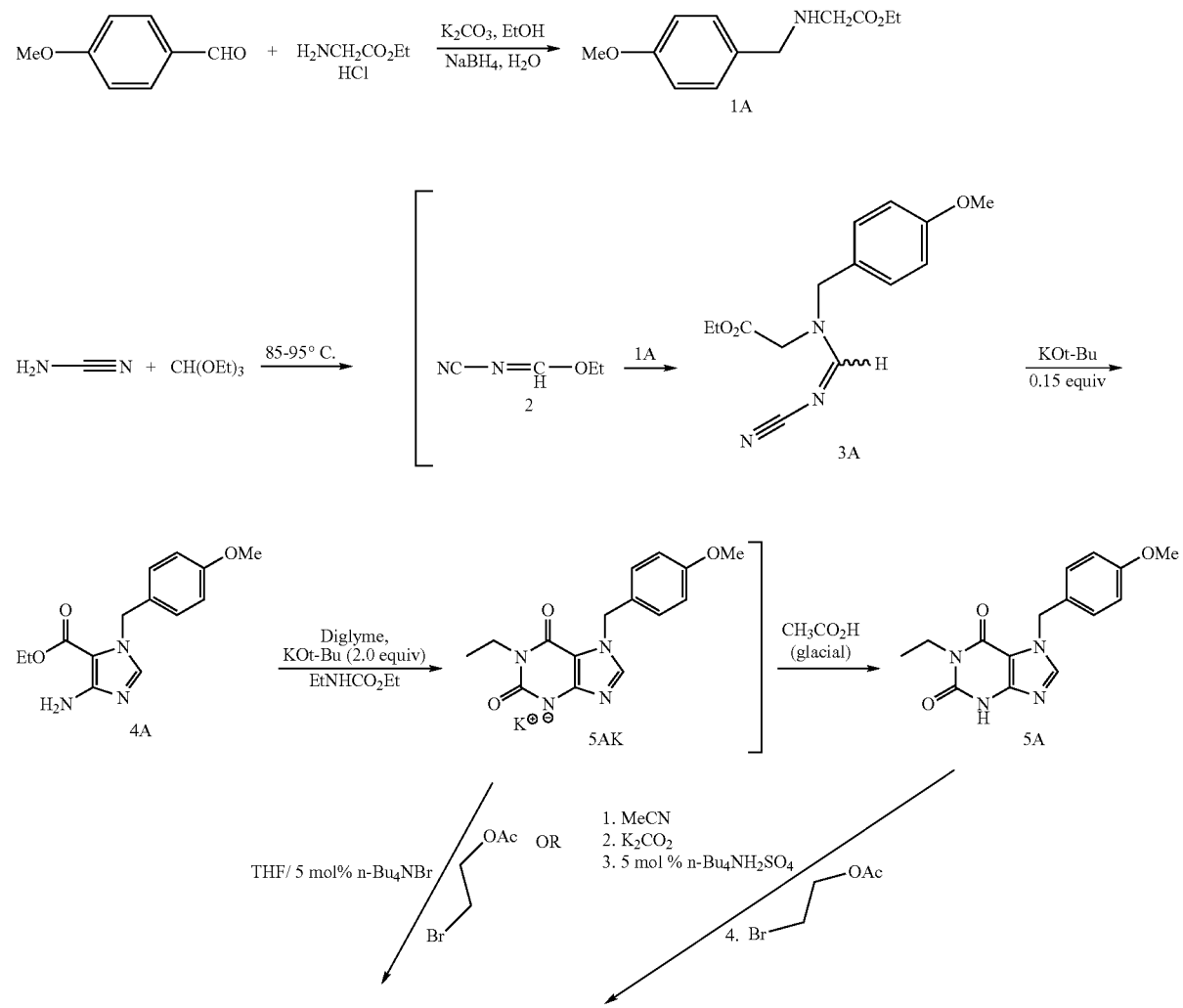

-continued

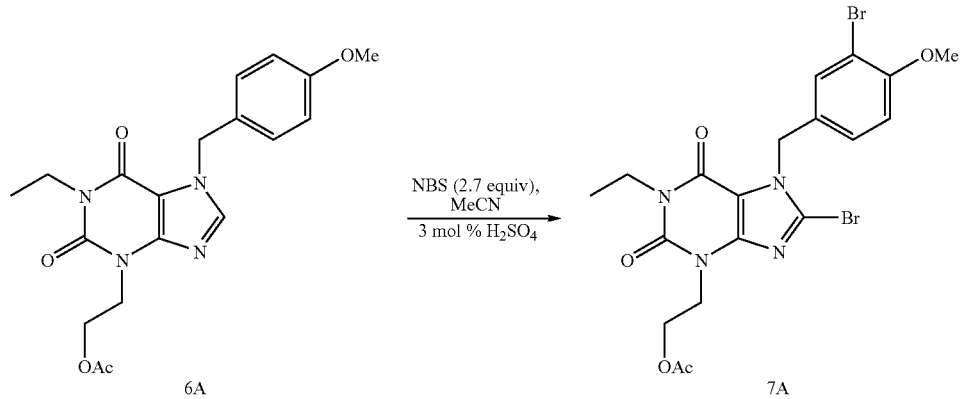

General Synthesis

One aspect of the invention comprises a general synthesis of Compound C from Compound B.

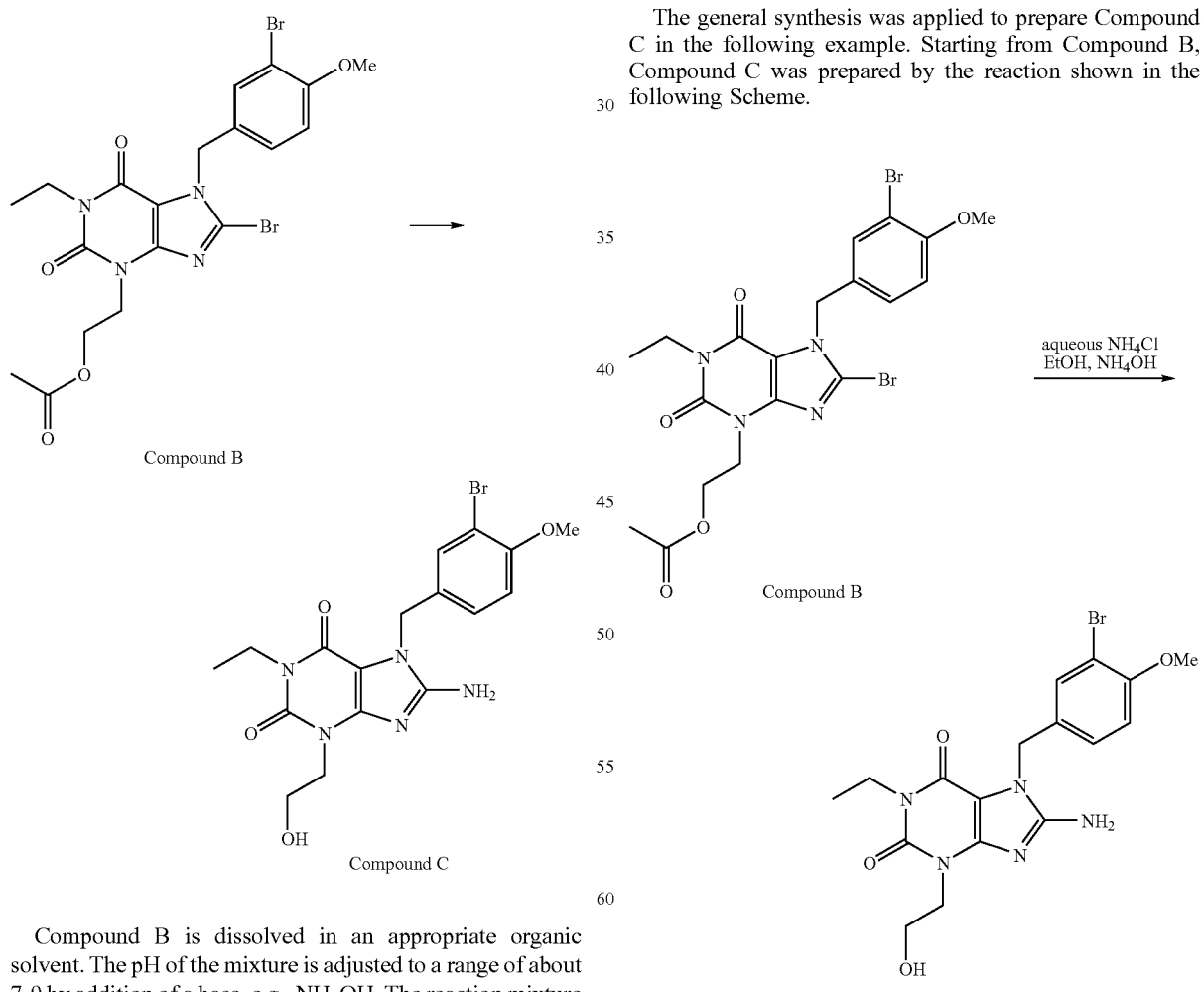

Compound B is dissolved in an appropriate organic solvent. The pH of the mixture is adjusted to a range of about 7-9 by addition of a base, e.g., NH₄OH. The reaction mixture is heated to a temperature range of about 150-170° C. in a sealed container for a period of about 6-12 days, then allowed to cool to room temperature. The reaction mixture is partitioned between a non-polar solvent and water. The organic layer is filtered and evaporated. Compound C is isolated.

Specific Synthesis

The general synthesis was applied to prepare Compound C in the following example. Starting from Compound B, Compound C was prepared by the reaction shown in the following Scheme.

Compound B (0.50 g, 0.92 mmol) was dissolved in ETOH (3 ml) and sat'd NH$_4$Cl (3 ml). A few drops of conc. NH$_4$OH were added such that the pH of the mixture was about 8. The reaction mixture was heated at about 160° C. in a sealed tube for 9 days, then allowed to cool to room temperature. The reaction mixture was partitioned between EtOAc and water. The aqueous layer was extracted with EtOAc, and the combined organic layers were dried (K$_2$CO$_3$), filtered and evaporated to give a residue. Column chromatography was used to purify Compound C. Subjection of the residue to column chromatography (SiO$_2$; gradient 2:98-4:96 MeOH/CH$_2$Cl$_2$) gave the product (0.19 g). The isolated Compound C had the following characteristics: MS m/z 438 (M+H); $^1$HNMR (CDCl$_3$, 400 MHz): δ 7.50 (1H, m), 7.25 (1H, m), 6.90 (1H, m), 5.29 (2H, s), 4.42 (2H, m), 4.30 (2H, m), 4.06 (2H, m), 3.96 (2H, m), 3.89 (3H, s), 1.26 (3H, m).

Enzymatic Syntheses of Compound C from Compound A

Compound C can be enzymatically synthesized from Compound A. The synthesis of Compound A is disclosed in U.S. patent application Ser. No. 09/940,760, which teaches the following reaction pathway (in which Compound A is labeled "13"):

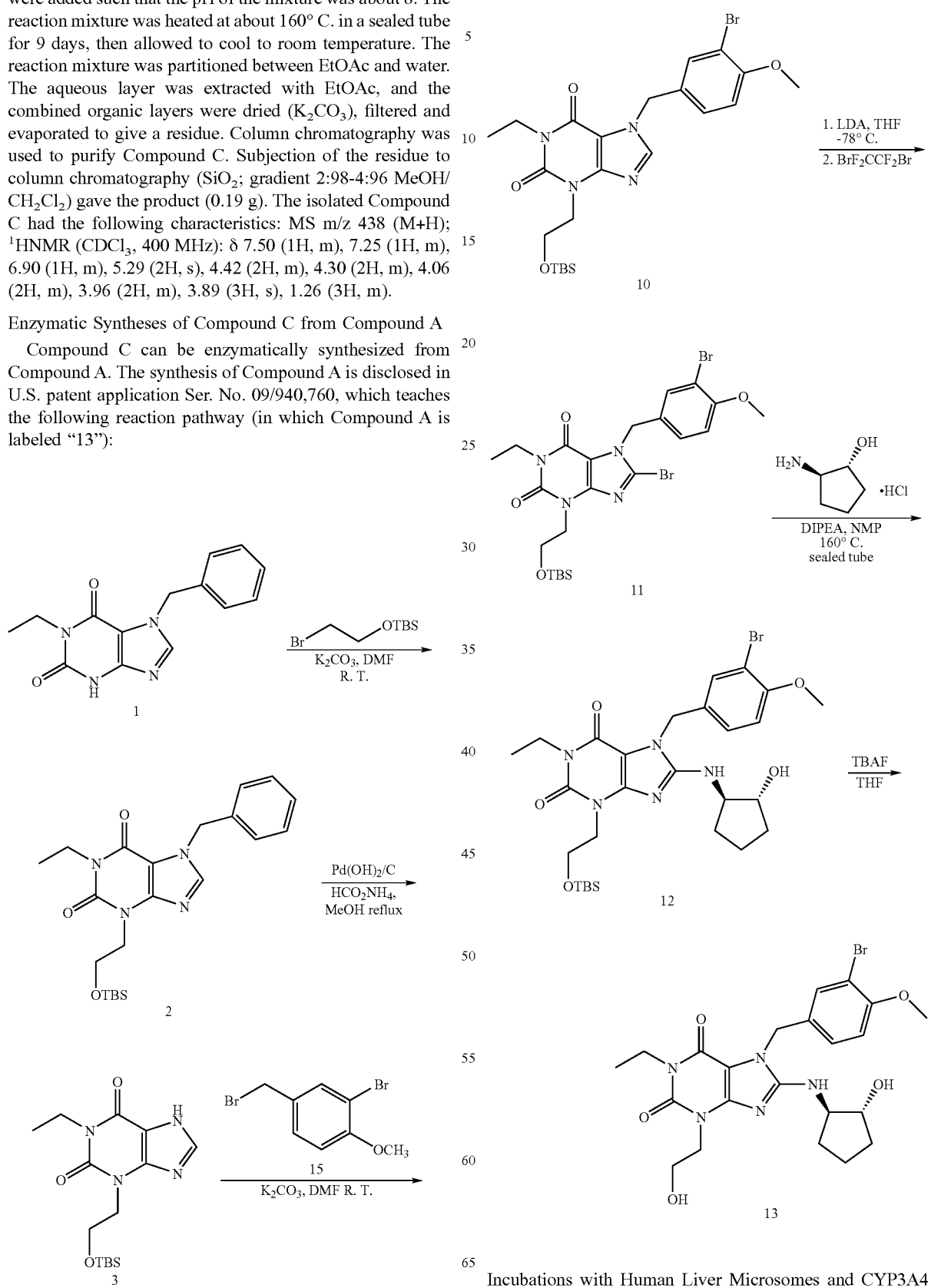

Incubations with Human Liver Microsomes and CYP3A4 SUPERSOMES™

Compound C was prepared via a biotransformation from Compound A. In vitro incubations of Compound A (1, 5 and 50 μM) were performed with pooled human liver microsomes and CYP3A4 SUPERSOMES®. This radiolabel allowed tracking of all the metabolites of Compound A. For this procedure, Compound A was synthesized by inserting a $^{14}C$ in the 4 position as indicated in the ring member numbering scheme below.

Ring Member Numbering Scheme of Compound A

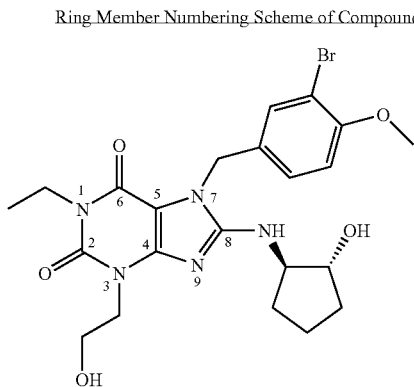

Incubation mixtures contained cytochrome P450 (1 nmol/mL for human liver microsomes or 0.2 nmol/mL for CYP3A4), β-NADP+ (1 mM), glucose-6-phosphate (5 mM), glucose-6-phosphate dehydrogenase (1.5 units/mL) and 3 mM magnesium chloride in 0.5 mL of 50 mM potassium phosphate buffer (pH 7.4). Prior to the addition of drug, incubation mixtures were pre-incubated for 3 min at about 37° C. Reactions were initiated by addition of drug, allowed to proceed for 120 min at about 37° C., and then terminated by the addition of about 0.25 mL of ice-cold methanol. The incubation mixture was vortexed and centrifuged (10,010 g) at about 4° C. for 10 min; supernatants were analyzed by HPLC and Liquid Chromatography Mass Spectrometry ("LC-MS"). Boiled human liver microsomes and incubations without NADPH served as negative control. A discussion of HPLC is provided in "HPLC in Pharmaceutical Analysis," vol. I, G. Szepesi (1990). A discussion of mass spectrometry is provided in "Remington: The Science and Practice of Pharmacy," 20$^{th}$ Ed., D. Limmer, ed., pp. 636-639 (2000).

Figure 2:
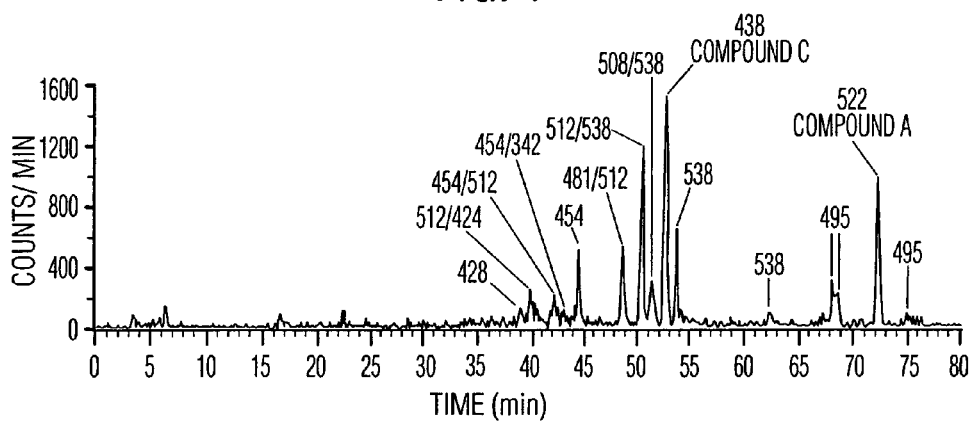
FIG. 2 shows a radiometric profile of the incubated drug and metabolites following a 120 min. incubation of Compound A with Human Liver Microsome and a NADPH-generating system.
Figure 3:
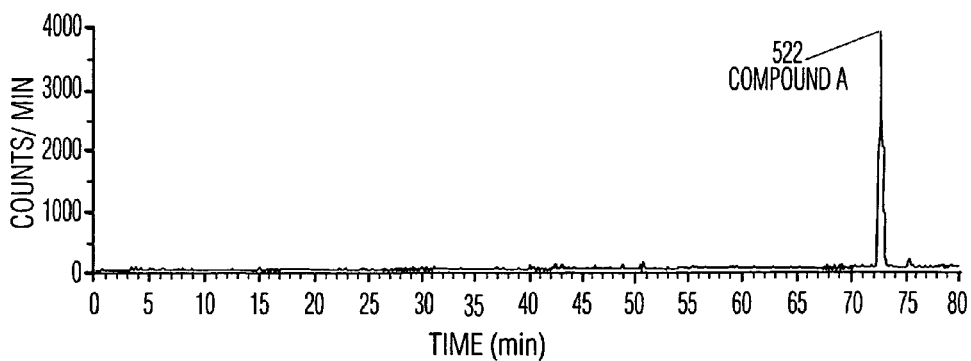
FIG. 3 shows a radiometric profile of the incubated drug and metabolites following a 120 min. incubation of Compound A with Control Insect Microsomes and a NADPH-generating system.

Compound A (1, 5, and 50 μM) was metabolized extensively when incubated with human liver microsomes (1 nmol/mL) in the presence of NADPH-generating system. Radiometric profiles of metabolites following 120 min incubation of Compound A (50 μM) with CYP3A4, Human Liver Microsomes, and Insect Microsomes, all with a NADPH-generating system, are shown in FIGS. 1, 2, and 3, respectively. In these figures, the y-axis reflects radioactivity of the eluted species and has units of counts per minute, while the x-axis reflects time of elution and has units of minutes. Each peak represents one or more compounds, and each of the more significant peaks is labeled with the mass-to-charge ratio value (m/z) of that compound. Mass-to-charge ratios are measured by mass spectrometry.

Compounds A and C are represented by the peaks labeled with the mass-to-charge ratios of 522 and 438, respectively. Compound C is a significant metabolite following incubations in both cases, as indicated by the prominence of these peaks in FIGS. 1 and 2. FIG. 3 represents the distribution of metabolites that results from incubation of Compound A with Control Insect Microsomes. The fact that the only substantial peak shown in FIG. 3 corresponds to that of Compound A (labeled with the mass-to-charge ratio of 522) indicates that no major metabolite formation was observed.

Derivatives of Compound C

Certain derivatives of Compound C are also within the scope of the present invention. Such derivatives can be described by the following structure:

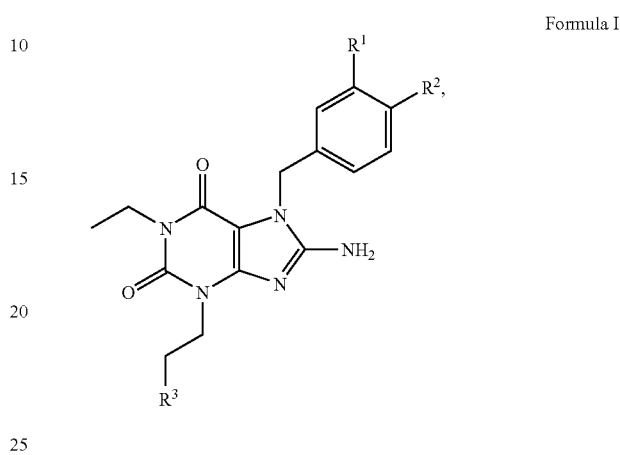

Formula I wherein $R^1$ $R^2$ and $R^3$ are independently selected from the group consisting of H, OH, OR$^4$, F, Cl, Br, NH$_2$, NHR$^4$, (NR$^4$)$_2$, —COOH, and —CONH$_2$ and R$^4$ is independently selected from the group consisting of H, —CH$_3$, —C$_2$H$_5$, isopropyl, and n-C$_3$H$_7$. In each of the occurrences of $R^1$ $R^2$ and $R^3$ in the structural formula above, the selection of any one group is made independently from the selection made for any other occurrence. Thus, for example, $R^1$ may be Br, $R^2$ may be NH$_2$ and $R^3$ may be —OH in the same molecule. Similarly, the selections of R$^4$ are independent of all other selections of R$^4$.

Such derivatives can be prepared by methods disclosed in, for example, U.S. patent application Ser. No. 09/940,760 and U.S. Pat. Nos. 5,939,419 and 5,393,755, and as would otherwise be know to one skilled in the art. Based on the similarity of the derivatives to Compound C, it is anticipated that many of these compounds would have similar effectiveness, e.g., as PDE 5 inhibitors.

Analytic Separation

Separations of Compound C from the samples were performed on a HPLC system (Alliance Model 2690; Waters Corp., Milford, Mass.), equipped with a Model 996 Photodiode Array Detector (Waters Corp.), and Model 500TR Radioactivity Detector (Packard Instrument Co., Meriden, Conn.). Separations were achieved on a 5-μm C18-A Polaris® 250×4.6 mm column (MetaChem Technologies, Torrance, Calif.) maintained at about 40° C. The mobile phase consisted of 10 mM ammonium acetate adjusted to pH 5.0 and acetonitrile with 0.1% acetic acid. Gradient elution of metabolites was achieved using programmed linear changes in mobile phase composition as summarized in the following.

TABLE A

| Time (min) | % Ammonium Acetate | % Acetonitrile/ Acetic Acid |
|---|---|---|
| 0.00 | 99.0 | 1.0 |
| 5.00 | 99.0 | 1.0 |
| 40.00 | 74.0 | 26.0 |

TABLE A-continued

| Time (min) | % Ammonium Acetate | % Acetonitrile/ Acetic Acid |
|---|---|---|
| 56.00 | 72.5 | 27.5 |
| 70.00 | 66.0 | 34.0 |
| 73.00 | 2.0 | 98.0 |
| 77.00 | 2.0 | 98.0 |
| 78.00 | 99.0 | 1.0 |
| 89.90 | 99.0 | 1.0 |

The flow rate was maintained at 1 mL/min and the eluant was monitored at 254 nm.

The recovery of radioactive material from HPLC column was 92.3% for active human liver microsomes. Incubations of 50 µM Compound A with cDNA-expressed CYP3A4 exhibited the greatest activity with respect to the formation of Compound C.

Inhibitions with Selective Chemical Inhibitors of CYP3A4

This experiment was performed in order to confirm the involvement of CYP3A4 in the biotransformation of Compound A. Inhibition of Compound A metabolism in human liver microsomes (1 nmol cytochrome P450/mL) was evaluated using ketoconazole (a selective inhibitor of CYP3A4). Human liver microsomes were pre-incubated separately with ketoconazole for 15 min at room temperature followed by the addition of buffer, cofactor, and substrate (50 µM). All incubations were performed as described under incubations with human liver microsomes. Incubation volumes were 0.5 mL and the final concentration of the organic solvents in the incubation system was 1% (v/v). Reactions were initiated by addition of substrate, allowed to proceed for 120 min at about 37° C., and then terminated by the addition of 0.25 mL of ice-cold methanol. The incubation mixture was vortexed and centrifuged (10,010 g) at about 4° C. for 10 min; supernatants were further analyzed by HPLC and LC-MS.

The results of the chemical inhibition studies showed that ketoconazole (CYP3A4 inhibitor) inhibited formation of all major metabolites by 73-84%. This experiment confirms the involvement of CYP3A4 in the metabolism of Compound A.

LC-MS/Radiometric Analysis

A HPLC system (Shimadzu Corporation, Kyoto, Japan) coupled with a QSTAR/Pulsar® LC-MS (QTOF) mass spectrometer (PE Biosystem, Concord, Ontario, Canada) and a Model 500TR radiometric detector (Packard Instrument Co., Meriden, Conn.) was used for the LC-MS/radiometric and LC-MS/MS/radiometric experiments. The QSTAR mass spectrometer was equipped with a turbo ion spray source and was nominally operated under the conditions listed in Table B.

TABLE B

| Parameters | Setting |
|---|---|
| Ionization Mode | Positive |
| IonSpray Voltage | 4.8 kV |
| TurboProbe Temperature | 350° C. |
| Curtain Gas | 50[a] |
| Ion Source Gas 1(Nebulizer Gas) | 40[a] |
| Ion Source Gas 2 (Heater Gas) | 70[a] |
| Collision Gas | 4[a] |
| Collision Energy | 32 |

[a]All gas parameter settings are arbitrary units.

The components of LC system coupled to the QSTAR mass spectrometer are summarized as follows in Table C:

TABLE C

| HPLC Components | Model and Vendor |
|---|---|
| System Controller | Model SCL-10A VP (Shimadzu Corporation, Kyoto, Japan) |
| Liquid Chromatographs | Model LC-10AD VP (Shimadzu Corporation) |
| Degasser | Model DGU-14A (Shimadzu Corporation) |
| UV-VIS Detector | Model SPD-10AV VP (Shimadzu Corporation) |
| Auto Injector | Model SIL-10AD VP (Shimadzu Corporation) |
| Column Oven | Model CTO-10A VP (Shimadzu Corporation) |

The LC conditions (such as gradient program, the analytical column, and column temperature) used for the Shimadzu LC system are the same as described previously for the Waters Alliance LC system. A Polaris C18-A MetaGuard® column was used to protect the analytical column during LC-MS analysis. The LC flow rate was 1 mL/min with approximately 27% diverted to the QSTAR mass spectrometer and rest to the radiometric detector.

Figure 4:
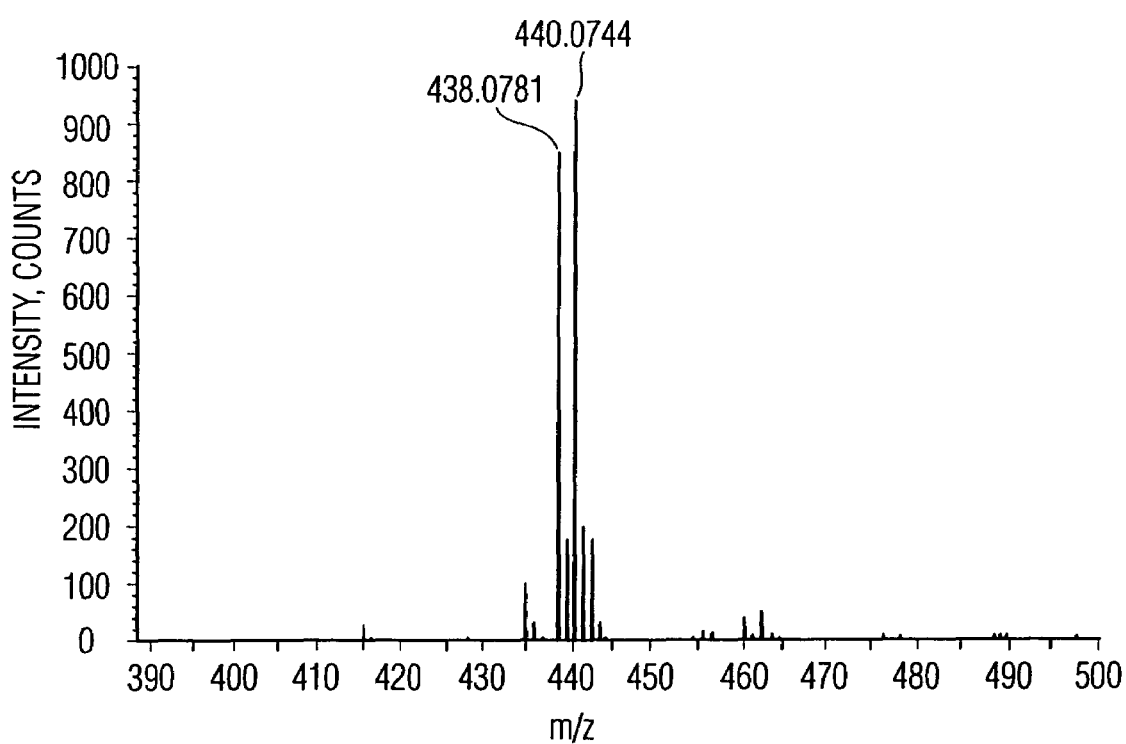
FIG. 4 shows a mass spectrum of Compound C that was prepared from an incubation of Compound A and CYP3A4.

The resulting LC-MS spectrum of the peak labeled 438, representing an isolated form of Compound C, is shown in FIG. 4. In FIG. 4, the y-axis reflects intensity in units of counts, and the x-axis reflects the mass-to-charge ratio, m/z. The displayed pattern of peaks is a function of the distribution of isotopes of Br (as $^{79}$Br and $^{81}$Br) in Compound C.

Forms of Compound C

Compound C, its derivatives, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of Compound C as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of Compound C, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prod rugs of the inventive compounds.

Formulations

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington: The Science and Practice of Pharmacy, 20th Edition, Lippincott Williams & Wilkins, Baltimore, Md. (2000).

Liquid form preparations include solutions, suspensions and emulsions. Examples of such preparations include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g., nitrogen.

Also included are solid form preparations, which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

The compound can be administered orally.

The pharmaceutical preparation can be in a unit dosage form. In such form, the preparations subdivided into suitably sized unit doses containing appropriate quantities of the active component, e.g., an effective amount to achieve the desired purpose.

The quantity of active compound in a unit dose of preparation may be varied or adjusted from about 0.01 mg to about 4000 mg, preferably from about 0.02 mg to about 1000 mg, more preferably from about 0.03 mg to about 500 mg, and most preferably from about 0.04 mg to about 250 mg according to the particular application.

The actual dosage employed may be varied depending upon the requirements of the patient and the severity of the condition being treated. Determination of the proper dosage regimen for a particular situation is within the skill in the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses.

Prodrugs

The present invention also encompasses the administration of any prodrug or precursor compound that, after being administered to a patient, may be metabolized in vivo to form a compound otherwise herein described. The term "prodrug", as employed herein, denotes a compound that is a drug precursor which, upon administration to a subject, undergoes chemical conversion by metabolic or chemical processes to yield Compound C or a salt and/or solvate thereof. A discussion of prodrugs is provided in T. Higuchi and V. Stella, *Pro-drugs as Novel Delivery Systems*, Volume 14 of the A.C.S. Symposium Series (1987) and in *Bioreversible Carriers in Drug Design*, Edward B. Roche, ed., American Pharmaceutical Association and Pergamon Press (1987), both of which are incorporated herein by reference thereto. Such a prodrug may be Compound A or any other compound that metabolizes in vivo to form Compound C.

It will be appreciated by those skilled in the art that changes could be made to the embodiments described above without departing from the broad inventive concept thereof. It is understood, therefore, that this invention is not limited to the particular embodiments disclosed, but is intended to cover modifications that are within the spirit and scope of the invention, as defined by the appended claims.

What is claimed is:

1. A compound of the following structure:

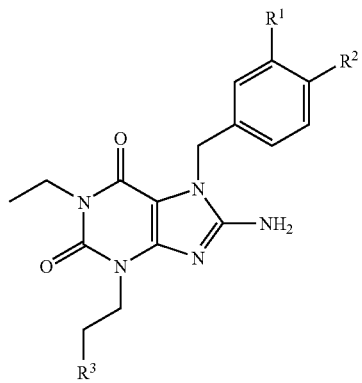

Formula I or a pharmaceutically acceptable salt, or ester thereof, wherein $R^1$, $R^2$ and $R^3$ are independently selected from the group consisting of H, OH, $OR^4$, F, Cl, Br, $NH_2$, $NHR^4$, $(NR^4)_2$, —COOH, and —$CONH_2$ and $R^4$ is independently selected from the group consisting of H, —$CH_3$, —$C_2H_5$, isopropyl, and normal-$C_3H_7$.

2. The compound of claim 1 wherein $R^1$ is Br.

3. The compound of claim 1 wherein $R^2$ is —OMe.

4. The compound of claim 1 wherein $R^3$ is OH.

5. An isolated and purified form of the compound of claim 1.

6. A pharmaceutical composition comprising a therapeutically effective amount of a compound of claim 1 in combination with a pharmaceutically acceptable carrier.

7. A method for elevating a cGMP level in a patient in need of the elevation of the cGMP level, comprising administering to the patient an effective amount of the compound according to claim 1.

8. A method for treating an erectile dysfunction in a patient in need of the treatment, comprising administering to the patient an effective amount of the compound according to claim 1.

9. A compound of the following structure:

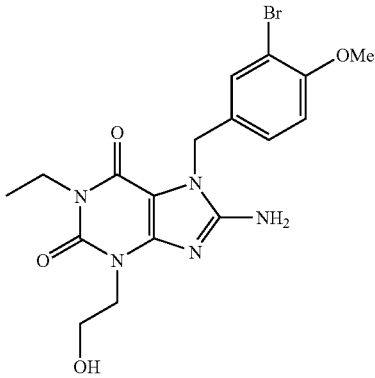

or pharmaceutically acceptable salts or esters thereof.

10. An isolated and purified form of the compound of claim 9.

11. A pharmaceutical composition comprising a therapeutically effective amount of a compound of claim 9 in combination with a pharmaceutically acceptable carrier.

12. A method for elevating a cGMP level in a patient in need of the elevation of the cGMP level, comprising administering to the patient an effective amount of the compound according to claim 9.

13. A method for treating an erectile dysfunction in a patient in need of the treatment, comprising administering to the patient an effective amount of the compound according to claim 9.

14. A process for producing the compound of claim 9, comprising reacting a solution of Compound B:

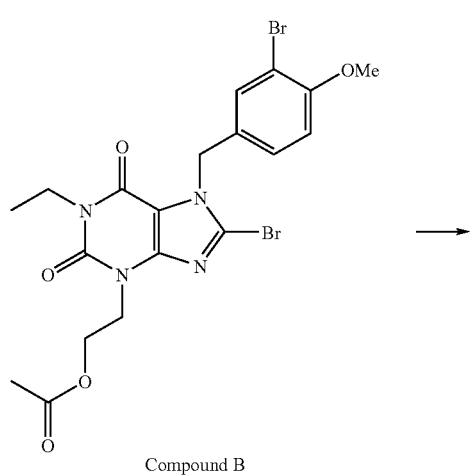
Compound B

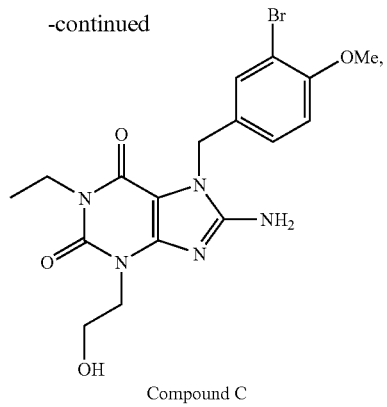
Compound C comprising the steps of:
  dissolving Compound B in an organic solvent;
  adding NH$_4$OH to the solution to obtain a pH range of about 7 to about 9; and
  heating the solution a temperature range of about 150 to about 170° C. for a time period of about 6 to about 12 days.

15. A process for producing the compound of claim 9 by reacting a solution of Compound B in EtOH and aqueous NH$_4$Cl in the presence of NH$_4$OH:

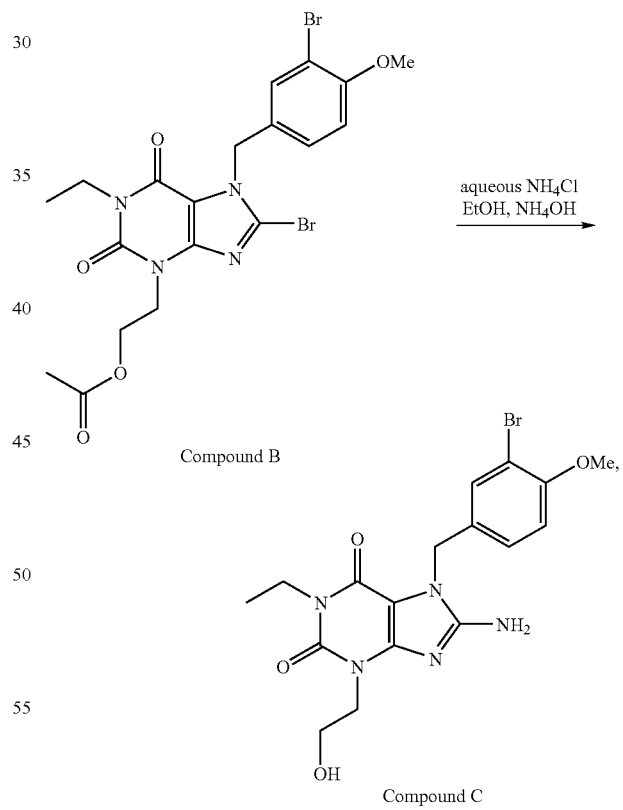
Compound B

Compound C comprising the steps of:
  dissolving Compound B in EtOH and saturated NH$_4$Cl;
  adding NH$_4$OH to the solution to obtain a pH of about 8; and
  heating the solution to about 160° C. for about 9 days.

* * * * *